United States Patent
Chen et al.

(10) Patent No.: US 9,116,101 B2
(45) Date of Patent: Aug. 25, 2015

(54) EXTENDED DEPTH OF FIELD MICROSCOPE SYSTEM

(75) Inventors: Yung-Lin Chen, Yunlin County (TW); Hsin-Yueh Sung, New Taipei (TW); Chir-Weei Chang, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 633 days.

(21) Appl. No.: 13/354,339

(22) Filed: Jan. 20, 2012

(65) Prior Publication Data

US 2013/0120550 A1    May 16, 2013

(30) Foreign Application Priority Data

Nov. 15, 2011    (TW) .............................. 100141603 A (51) Int. Cl.
  *G01N 21/00* (2006.01)
  *G01N 21/17* (2006.01)
  *G02B 27/00* (2006.01)
  *G02B 21/36* (2006.01)

(52) U.S. Cl.
  CPC .............. *G01N 21/17* (2013.01); *G02B 21/367* (2013.01); *G02B 27/0075* (2013.01)

(58) Field of Classification Search
  CPC .. G02B 21/365; G02B 21/367; G02B 21/002; H04N 7/18; G01N 21/6458
  USPC .......................................................... 348/79
  See application file for complete search history.

(56) References Cited

U.S. PATENT DOCUMENTS

| 4,875,012 | A  | 10/1989 | Maeda et al. |
| 5,278,757 | A  | 1/1994  | Hoctor et al. |
| 5,615,048 | A  | 3/1997  | Davies et al. |
| 6,011,874 | A  | 1/2000  | Gluckstad |
| 6,097,856 | A  | 8/2000  | Hammond, Jr. |
| 6,873,733 | B2 | 3/2005  | Dowski, Jr. |
| 7,115,849 | B2 | 10/2006 | Dowski, Jr. et al. |
| 7,224,540 | B2 | 5/2007  | Olmstead et al. |

(Continued)

FOREIGN PATENT DOCUMENTS

| CN | 101846798 | 9/2010 |
| CN | 102221746 | 10/2011 |
| EP | 2253985   | 11/2010 |
| TW | 201109735 | 3/2011 |
| TW | 201135345 | 10/2011 |

OTHER PUBLICATIONS

Wanli Chi and Nicholas George, "Electronic imaging using a logarithmic asphere", Optics Letters, vol. 26, Issue 12, pp. 875-877 (2001).

(Continued)

*Primary Examiner* — Jay Au Patel
*Assistant Examiner* — Frank Huang
(74) *Attorney, Agent, or Firm* — Jianq Chyun IP Office (57) ABSTRACT

An extended depth of field microscope system for phase object detection includes an imaging optical module and a phase/intensity converting module. The imaging optical module has an object lens group, in which an axial symmetric phase coding is added, to produce an axial symmetric spherical aberration. A point spread function (PSF) and an image with extended depth of field can be obtained with a predetermined level of similarity. The phase/intensity converting module converts the phase change of the light passing the phase object, into an image light with change of light intensity.

15 Claims, 6 Drawing Sheets (56) References Cited

U.S. PATENT DOCUMENTS

| | | | |
|---|---|---|---|
| 7,260,251 | B2 | 8/2007 | Dowski, Jr. et al. |
| 7,312,432 | B2 | 12/2007 | Liang |
| 7,385,705 | B1 | 6/2008 | Hoctor et al. |
| 7,450,745 | B2 | 11/2008 | Dowski, Jr. et al. |
| 7,453,653 | B2 | 11/2008 | Dowski, Jr. et al. |
| 7,547,874 | B2 | 6/2009 | Liang |
| 7,626,769 | B2 | 12/2009 | Olmstead et al. |
| 7,646,549 | B2 | 1/2010 | Zalevsky et al. |
| 7,812,295 | B2 | 10/2010 | Zalevsky et al. |
| 2003/0173502 | A1* | 9/2003 | Dowski et al. ............... 250/216 |
| 2011/0032608 | A1* | 2/2011 | Suenaga ..................... 359/386 |
| 2011/0050980 | A1 | 3/2011 | Sung et al. |
| 2011/0249028 | A1* | 10/2011 | Chang et al. ................. 345/643 |

OTHER PUBLICATIONS

"Office Action of Taiwan Counterpart Application", issued on Feb. 21, 2014, p. 1-p. 7, in which the listed references were cited.

Sara C. Tucker, et al., "Extended depth of field and aberration control for inexpensive digital microscope systems", Optics Express, vol. 4, 1999, 467-474.

Xinping Liu, et al., "Extended depth of field of microscope objective for particle tracking", SPIE, vol. 5524, 2004, 436-443.

Pantazis Mouroulis, et al., "Depth of field extension in a low power microscope objective", SPIE, vol. 7429, 2009, 742904-1-742904-11.

Nicolas Caron, et al., "Polynomial phase masks for extending the depth of field of a microscope", Applied Optics, vol. 47, 2008, E39-E43.

E.J. Botcherby, et al., "Scanning two photon fluorescence microscopy with extended depth of field", Optics Communications, 2006, 253-260.

Zhi-Li Zhang, et al., "Quantitative measurement of transparent object," Optical Technique, vol. 27, No. 2, Mar. 2001, pp. 146-pp. 149.

Jun-Tang Cheng, "Differential Interference Contrast Microscopy," Optical Instruments, vol. 1, No. 6, Dec. 1984, pp. 1-pp. 17.

"Office Action of China Counterpart Application", issued on Jul. 17, 2014, p. 1-p. 8, in which the listed references were cited.

* cited by examiner

EXTENDED DEPTH OF FIELD MICROSCOPE SYSTEM

CROSS-REFERENCE TO RELATED APPLICATION

This application claims the priority benefit of Taiwan application serial no. 100141603, filed on Nov. 15, 2011. The entirety of the above-mentioned patent application is hereby incorporated by reference herein and made a part of this specification.

TECHNICAL FIELD

The disclosure relates to a microscope system, which is capable of imaging a phase object.

BACKGROUND

A phase object, such as a cell object, is transparent to light. However, the light may have a phase variation due to an internal structure of the phase object. Therefore, to obtain the internal structure of the phase object, the phase variation of the light is required to be detected for converting into image contrast. Namely, the image of the phase object is formed as the light passing through the phase object to generate bright and dark contrast due to an optical path difference.

Regarding a design of a microscope, the depth of field is usually quite short due to a large numerical aperture (NA). Moreover, although a confocal microscope may have effect to extend field depth, it takes long time for multiple imaging processes at different depths, causing low speed. Although the depth of field can be extended by reducing the aperture, light flux would decrease.

A present microscope system for phase object approximately has a phase contrast structure, a transmissive differential interference contrast (DIC) structure, or a reflective DIC structure. An image of a conventional microscope system for phase object maintains a high resolution only within a range of the depth of field, and the resolution of the image is severely decreased beyond the range of depth of field. In order to extend the depth of field, the conventional structure is added with a phase device to code a wavefront through a non-axial symmetric method.

Since the structure of phase device is non-axial symmetric, it is difficult to process the phase device, and the geometric structure in fabrication has a low accuracy. Besides, the generated point spread function (PSF) being generated is non-axial symmetric, which may increase difficulty in image restoration.

SUMMARY

The disclosure is directed to a microscope system for phase object, which is a microscope system with an extended depth of field, and an axial symmetric phase coding device is added at an exit pupil of the microscope system. The wavefront of the exit pupil generates an axial symmetric spherical aberration.

The disclosure provides an extended depth of field microscope system for phase object including an optical imaging module and a phase/intensity converting module. An axial symmetric phase coding is added to an objective lens group of the optical imaging module to produce an axial symmetric spherical aberration. A point spread function (PSF) and an image with extended depth of field can be obtained with a predetermined level of similarity. The phase/intensity converting module converts a phase variation of light passing through a phase object into an image light with light intensity variation. The phase variation is caused by optical path difference when passing the phase object.

The disclosure provides an extended depth of field microscope system for phase object including an optical imaging module, a phase/intensity converting module, a photoelectric converting device and an image restoration module. An axial symmetric phase coding is added to an objective lens group of the optical imaging module to produce an axial symmetric spherical aberration. A point spread function (PSF) and an image with extended depth of field can be obtained with a predetermined level of similarity. The phase/intensity converting module converts a phase variation of light passing through a phase object, caused by optical path difference, into an image light with light intensity variation. The photoelectric converting device receives and converts the image light to obtain a digital image. The image restoration module is connected to the photoelectric converting device for restoring the digital image into a clear image.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF DISCLOSED EMBODIMENTS

The disclosure provides an axial symmetric phase coding method, which is adapted to a microscope system for phase object. For example, in a biomedical application, a wavefront at an exit pupil of an optical imaging module is an axial symmetric wavefront with extended depth of field. Such wavefront is a combination of a plurality of spherical aberration terms with a characteristic of axial symmetry, to have effect of high similarity of a point spread function (PSF) and an image with extended depth of field. In detail, the spherical aberration terms at least include a third-order spherical aberration term, which represents a spherical wavefront function of an $r^4$ term, where r is a distance relative to a central axis. A third-order is obtained by differentiating the $r^4$ spherical aberration term, which is the so-called third-order spherical aberration term. The other higher odd number-order spherical aberration terms have a similar definition.

Since a structure of a phase coding device is axial symmetric, fabrication accuracy of the phase coding device can be greatly improved, which allows a simple fabrication process and low cost. Besides, since the PSF is axial symmetric, difficulty in image restoration is reduced, and since the phase coding device is axial symmetric, the phase distribution can be distributed and integrated to a lens design without using an additional phase device.

Embodiments are provided below to describe the disclosure, though the disclosure is not limited to the provided embodiments, and the provided embodiments can be suitably combined.

Figure 1:
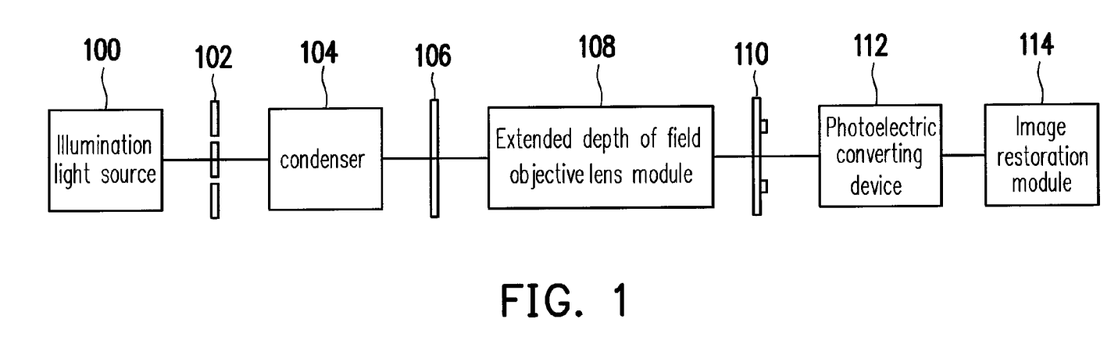
FIG. 1 is a schematic diagram of a microscope system for phase object of a phase contrast structure according to an embodiment of the disclosure.
Figure 5:
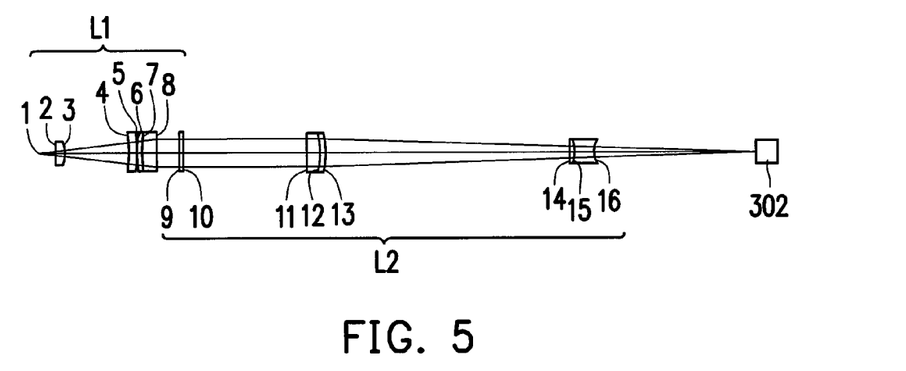
FIG. 5 is a schematic diagram of a microscope system with extended depth of field and without an additional phase device according to an embodiment of the disclosure.
Figure 6:
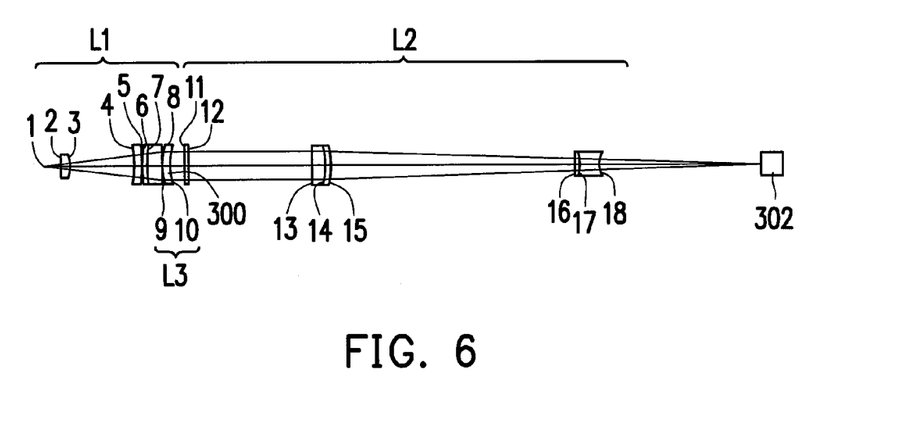
FIG. 6 is a schematic diagram of a microscope system with extended depth of field and an additional phase device according to an embodiment of the disclosure.

FIG. 1 is a schematic diagram of a microscope system for phase object of a phase contrast (PC) structure according to an embodiment of the disclosure. Referring to FIG. 1, an extended depth of field objective lens module 108 has a predetermined range of depth of field, and captures an image light of a phase object 106. In an embodiment, the extended depth of field objective lens module 108 includes an objective lens group with the predetermined range of depth of field, a tube lens group that receives the image light output by the objective lens group to form a gathered image light, and an axial symmetric phase coding device, which can be integrated with the objective lens group or disposed between the objective lens group and the tube lens group, so as to produce an axial symmetric spherical aberration. Detailed embodiments of the objective lens group, the tube lens group and the axial symmetric phase coding device are illustrated in FIG. 5 and FIG. 6. A photoelectric converting device 112 receives and converts the gathered image light output by the tube lens group to obtain a digital image. The image restoration module 114 can perform restoration processing on the image to improve image clarity. Since the aberration of the system is axial symmetric, the restoration processing is relatively easy.

Referring to FIG. 1, an illumination light source 100 is used to produce an illumination light onto the phase object 106. An annulus plate 102 is used to process the illumination light to produce an annular light. A condenser 104 is disposed between the illumination light source 100 and the phase object 106 to converge the illumination light onto the phase object 106.

A part of the annular light that passes through the phase object may form a diffraction light, which is slowed in speed and has a phase difference of 90 degrees with a direct passing light (another part of the annular light) that does not pass through the phase object. A phase ring 110 is disposed behind the extended depth of field objective lens module 108 to further advance the direct passing light by 90 degrees, and the diffraction light remains without change. In this way, the direct passing light and the diffraction light have a phase difference of 180 degrees, which may cause a destructive interference. As a result, an object image is darkened but a profile of the image is bright.

Figure 2:
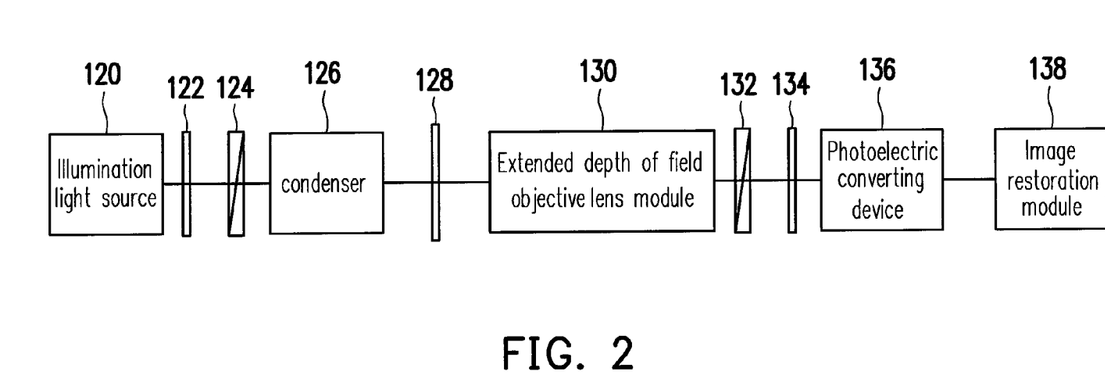
FIG. 2 is a schematic diagram of a microscope system for phase object of a transmissive differential interference contrast (DIC) structure according to an embodiment of the disclosure.

FIG. 2 is a schematic diagram of a microscope system for phase object of a transmissive differential interference contrast (DIC) structure according to an embodiment of the disclosure. Referring to FIG. 2, based on the transmissive DIC structure, the microscope system for phase object includes an illumination light source 120, a polarizer 122, a prism element 124, a condenser 126, a phase object 128, an extended depth of field objective lens module 130, a prism element 132, a analyzer 134, a photoelectric converting device 136 and an image restoration module 138.

The polarizer 122 is disposed behind the illumination light source 120 for linearly polarizing the illumination light. The prism element 124 is disposed between the condenser 126 and the polarizer 122, and the prism element 124 is, for example, a Wollaston prism, which can split the linearly polarized light into two polarized lights orthogonal to each other. Phases of the two polarized lights are the same in the beginning. After the two polarized lights pass through the phase object 128, the two polarized lights have an optical path difference due to different thickness and refractive indices of the phase object 128. The phase object 128 is imaged through the extended depth of field objective lens module 130. The prism element 132 is disposed behind the extended depth of field objective lens module 130 to combine the two polarized lights orthogonal to each other. Finally, the lights pass through the analyzer 134, and the two orthogonal polarized lights are converted into the linearly polarized light, and the two lights are interfered. When the optical path difference is 0, none light passes through the analyzer 134, and when the optical path difference is ½λ, the light passing through, the analyzer 134 reaches a maximum value. A contrast between bright and dark is produced. The photoelectric converting device 136 converts the image light into a digital image. The image restoration module 138 restores the image to improve image clarity.

Figure 3:
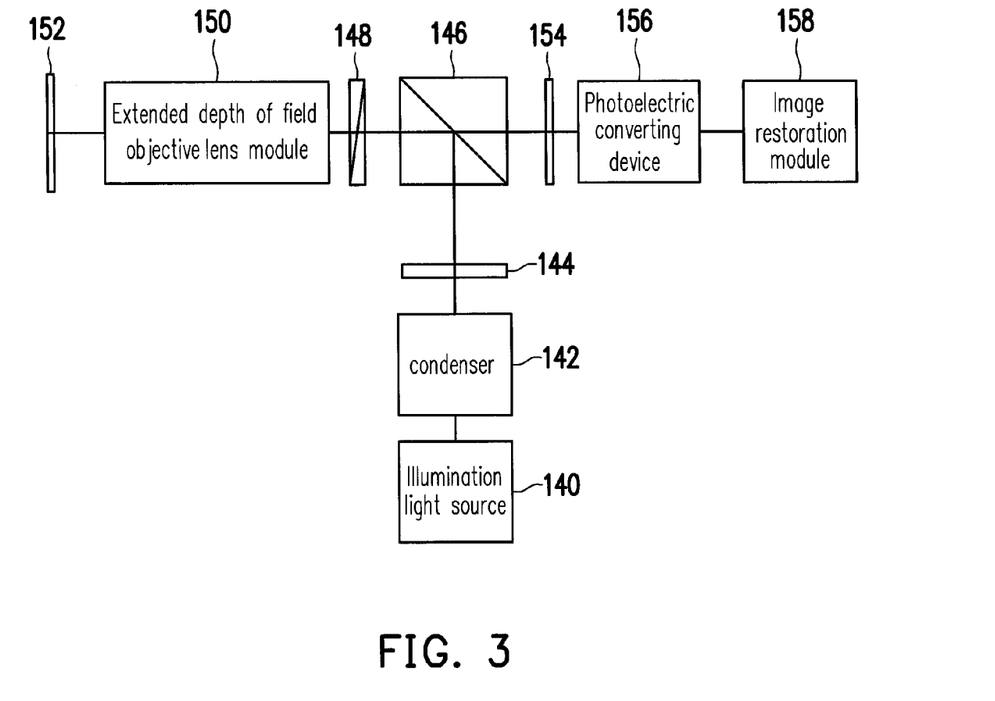
FIG. 3 is a schematic diagram of a microscope system for phase object of a reflective DIC structure according to an embodiment of the disclosure.

FIG. 3 is a schematic diagram of a microscope system for phase object of a reflective DIC structure according to an embodiment of the disclosure. Referring to FIG. 3, based on the reflective DIC structure, the microscope system for phase object may include an illumination light source 140, a condenser 142, a polarizer 144, a beam splitter 146, a prism element 148, an extended depth of field objective lens module 150, a phase object 152, a analyzer 154, a photoelectric converting device 156 and an image restoration module 158. The illumination light source 140 provides an illumination light. The condenser 142 converges the illumination light. The polarizer 144 linearly polarizes the light. The beam splitter 146 is disposed behind the polarizer 144, and is used for reflecting the linearly polarized light to the prism element 148. The prism element 148 splits the linearly polarized light into two polarized lights orthogonal to each other. Phases of the two polarized lights are the same in the beginning, and the two polarized lights pass through the extended depth of field objective lens module 150 to reach the phase object 152, and are reflected back to the extended depth of field objective lens module 150. The two polarized lights have an optical path difference due to different thickness and refractive indices of the phase object 152. The phase object 152 is imaged through an objective lens group of the extended depth of field objective lens module 150. The two polarized lights orthogonal to each other again pass through the prism element 148, and the prism element 148 combines the two polarized lights orthogonal to each other. Finally, the lights pass through the analyzer 154, and the two polarized lights orthogonal to each other are converted into the linearly polarized light, and the two lights are interfered. When the optical path difference is 0, none light passes through the analyzer 154, and when the optical path difference is ½λ, the light passing through the analyzer 154 reaches a maximum value. A contrast between bright and dark is produced.

An image of a conventional microscope system for phase object maintains a high resolution only within the range of depth of field, and the resolution of the image is greatly degreased beyond the range of depth of field. Referring to the embodiments illustrated in FIGS. 1-3, the microscope objective lens is designed as the depth of field extension microscope objective lens module to extend the depth of field. The image maintains to the high resolution in a larger range, and the imaging contrast effect is stronger.

Figure 4:
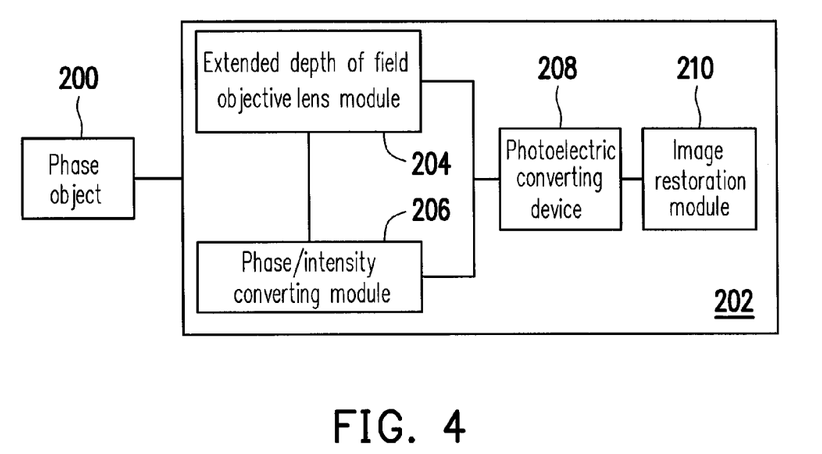
FIG. 4 is a functional block schematic diagram of a microscope system for phase object according to an embodiment of the disclosure.

FIG. 4 is a functional block schematic diagram of a microscope system for phase object according to an embodiment of the disclosure. Referring to FIG. 4, the microscope system for phase object 202 can capture an image of a phase object 200. An internal structure of the phase object 200 may produce a phase difference, so as to obtain a profile of the structure.

The microscope system for phase object 202 includes an extended depth of field objective lens module 204 and a phase/intensity converting module 206. Interaction of the two modules may achieve an image capturing capability with extended depth of field for the phase object 200. A transparent structure of the phase object 200 is presented by converting a phase variation of the light into an image light with light intensity variation. The light intensity of the image light is converted into a digital image gray level by the photoelectric converting device 208. Moreover, the image restoration module 210 further restores a clear image according to an actual requirement.

In other words, regarding the extended depth of field objective lens module 204, a phase coding design is added to an optical imaging module of the phase object to improve similarity of point spread functions (PSF) of different object distances, and the phase/intensity converting module 206 converts a phase difference of the light passing through the phase object into a light intensity difference to produce the bright and dark contrast, the coded light intensity difference image light is received by the photoelectric converting device 208, and in collaboration with digital image signal processing, the depth of field is extended only through single imaging without multiple layered imaging.

Regarding a theoretic design of the depth of field extension microscope objective lens module, the disclosure provides a method of adding an axial symmetric phase coding at an exit pupil of the microscope system. The wavefront of the exit pupil generates a spherical aberration. The spherical aberration of the disclosure can be obtained according to following equations (1)-(3), by which the spherical aberration and a depth of focus are deduced below:

$$\delta z = k \times \rho^2; \tag{1}$$

$$\delta z = -16(F/\#)^2 W_{040} \times \rho^2; \text{ and} \tag{2}$$

$$W(\rho) = \sum_{n=4,6,8...} \left(\frac{\delta z}{4n(F/\#)^2}\right)\left(-\frac{\delta z}{f_0}\right)^{\frac{n-4}{2}} \rho^n, \tag{3}$$

where, $\rho$ is a normalized aperture height of the exit pupil, $\delta z$ is a longitudinal spherical aberration or a depth of focus, $W_{040}$ is a third-order spherical aberration, W is a wavefront aberration, n is a order number of the spherical aberration, for example, n=4 is the third-order spherical aberration, $f_0$, is a paraxial focal length, and F/# is an F-number.

The spherical aberration of the disclosure can be obtained according to an axial irradiance equalization (AIE) phase coding equation. The AIE equation is as follows:

$$f(r) = \frac{f_0}{3} - \frac{(\sqrt[3]{2}(3r^2 - f_0^2))}{\left(3\left[2f_0^3 + 27Cr^2 + 18f_0r^2 + \sqrt{4(3r^2 - f_0^2)^3 + (2f_0^3 + 27Cr^2 + 18f_0r^2)^2}\right]^{1/3}\right)} + \frac{\left[2f_0^3 + 27Cr^2 + 18f_0r^2 + \sqrt{4(3r^2 - f_0^2)^3 + (2f_0^3 + 27Cr^2 + 18f_0r^2)^2}\right]^{1/3}}{2(\sqrt[3]{2})}, \tag{4}$$

Where, $f_0$ is a paraxial focal length, $\Delta z$ is a required range of a depth of focus, $R_{max}$ is a maximum exit pupil radius, r is an exit pupil radius, and C is defined as a following equation (5):

$$C = \frac{\Delta z[(R_{max})^2 + (f_0 + \Delta z)^2]}{(R_{max})^2}. \tag{5}$$

The aforementioned method of calculating the require aberration is deduced according to an optical theory, though the spherical aberrations required for extending the depth of field of the system that are provided by using an optimized design of even-order aspherical coefficients at least include the third-order spherical aberration term of n=4, and an equation (6) is used to represent various order spherical aberration terms of n=8:

$$Z(r) = \frac{cr^2}{1 + \sqrt{1 - (1+k)c^2r^2}} + ADr^4 + AEr^6 + AFr^8, \tag{6}$$

where Z(r) is an even-order aspherical formula, Z is a sag of phase device, r is an aperture height, c is a curvature, k is a conic coefficient, AD, AE and AF are even-order aspherical coefficients. In the even-order aspherical coefficients, at least the coefficient AD is not zero, and the coefficients AE and AF can be added according to an actual requirement, or higher-order spherical aberration terms can be added.

FIG. 5 is a schematic diagram of a microscope system with extended depth of field and without an additional phase device according to an embodiment of the disclosure. Referring to FIG. 5, the microscope system with extended depth of field and without the additional phase device includes an objective lens group L1, a tube lens group L2 and a image light processing unit 302 at a post end. In the present embodiment, the phase device required to generate the phase coding is formed by aspherical surfaces 4 and 5, and is integrated into the objective lens group L1 without using the additional phase device. The tube lens group L2 is a photoelectric converting device used for converging the imaged image light to the image light processing unit 302. Surface information of 16 positions of the present embodiment is shown in following Table 1 and Table 2, and coefficients in the Table 2 are the coefficients of the equation (6). Surfaces 2-8 of the objective lens group L1 are a microscope objective lens with a magnification of 10×, a numerical aperture (NA) of 0.25 and a focal length of 18 mm. Surfaces 9-16 of the tube lens group L2 are a tube lens with a focal length of 180 mm.

TABLE 1

| Surface No. | Radius of curvature (mm) | Thickness (mm) | Refractive index |
| --- | --- | --- | --- |
| 0(OBJ) | Infinity | 0.17 | 1.525 |
| 1 | Infinity | 5.011 | |
| 2 | −112.301 | 3.511 | 1.489 |
| 3 | −5.916 | 22.02 | |
| 4 | −124.428 | 2.412 | 1.628 |
| 5 | −40.695 | 0.309 | |
| 6 | 56.185 | 0.698 | 1.723 |
| 7 | 18.134 | 6 | 1.489 |
| 8 | −39.583 | 2.054 | |
| 9 | 64.44 | 1 | 1.531 |
| 10 | 66.726 | 43.665 | |
| 11 | 222.976 | 5.009 | 1.487 |
| 12 | −55.499 | 1 | 1.923 |
| 13 | −73.859 | 86.334 | |
| 14 | 148.087 | 1.221 | 1.834 |
| 15 | −37.093 | 7.706 | 1.607 |
| 16 | 32.508 | 55.674 | |
| 17(IMA) | Infinity | | |

TABLE 2

| even-order aspherical coefficients | | |
| --- | --- | --- |
| Surface No. | AD | AE |
| 4 | −6.4145804e−006 | −2.1937481e−009 |
| 5 | 1.9523485e−006 | −9.3112257e−011 |
| 9 | −3.5439868e−006 | −2.1039236e−006 |
| 10 | −3.1391532e−006 | −2.1517961e−006 |

FIG. 6 is a schematic diagram of a microscope system with extended depth of field and an additional phase device according to an embodiment of the disclosure. Referring to FIG. 6, the microscope system with extended depth of field and an additional phase device includes an objective lens group L1, a phase device L3, a tube lens group L2 and the image light processing unit 302 at the post end. In the present embodiment, the phase device required to generate the phase coding is formed by aspherical surfaces 9 and 10, which is assembled according to a requirement without influencing the objective lens group L1. The tube lens group L2 is a photoelectric converting device used for converging the imaged image light to the image light processing unit 302. Surface information of 18 positions of the present embodiment is shown in a following Table 3 and a Table 4, and coefficients in the Table 4 are the coefficients of the equation (6).

Surfaces 2-8 are the objective lens group L1 with a magnification of 10×, an NA of 0.25 and a focal length of 18 mm. Surfaces 9 and 10 are the phase device L3. Surfaces 11-18 are the tube lens group L2 with a focal length of 180 mm.

TABLE 3

| Surface No. | Radius of curvature (mm) | Thickness (mm) | Refractive index |
| --- | --- | --- | --- |
| 0(OBJ) | Infinity | 0.17 | 1.525 |
| 1 | Infinity | 5.011 | |
| 2 | −108.591 | 3.5 | 1.489 |
| 3 | −5.924 | 21.893 | |
| 4 | −126.498 | 2.4 | 1.628 |
| 5 | −41.041 | 0.3 | |
| 6 | 56.219 | 1.5 | 1.723 |
| 7 | 18.249 | 6 | 1.489 |
| 8 | −39.682 | 0.2 | |
| 9 | 18.043 | 2 | 1.531 |
| 10 | 17.436 | 5.586 | |
| 11 | 64.44 | 1 | 1.531 |
| 12 | 66.726 | 43.665 | |
| 13 | 222.976 | 5.009 | 1.487 |
| 14 | −55.499 | 1 | 1.923 |
| 15 | −73.859 | 86.334 | |
| 16 | 148.087 | 1.221 | 1.834 |
| 17 | −37.093 | 7.706 | 1.607 |
| 18 | 32.508 | 55.674 | |
| 19(IMA) | Infinity | | |

TABLE 4

| even-order aspherical coefficients | | |
| --- | --- | --- |
| Surface No. | AD | AE |
| 9 | −4.6614737e−005 | −4.9541858e−007 |
| 10 | −4.5517029e−005 | −5.9457234e−007 |
| 11 | −3.5439868e−006 | −2.1039236e−006 |
| 12 | −3.1391532e−006 | −2.1517961e−006 |

In the embodiment of the disclosure, the depth of focus range is, for example, δz=0.08 mm, and by adding the spherical aberration, the image captured by an array-type photoelectric converting device can be a specific blurred image, and due to the depth of field extension, the blurred image has a high similarity, and a spherical aberration coefficient thereof is as follows:

$$W_{040}{:}{-}2.608\lambda. \tag{7}$$

In the disclosure, the wavefront of the exit pupil includes at least the third-order spherical aberration, for example, the NA of the microscope objective lens is 0.25-0.4, and a high-order spherical aberration (fifth, seventh-order spherical aberration) is smaller than the third-order spherical aberration. When the NA of the microscope objective lens is greater than 0.4, a spherical aberration combination of the wavefront of the exit pupil at least includes the third-order spherical aberration term, and the high-order spherical aberration terms such as the fifth-order and the seventh-order spherical aberration terms can also be added. As known by those skilled in the art, the odd number-order spherical aberration term refers to a spherical aberration order number of the spherical aberration term with n of an even number in the equation (3) obtained after differentiation.

Figure 7:
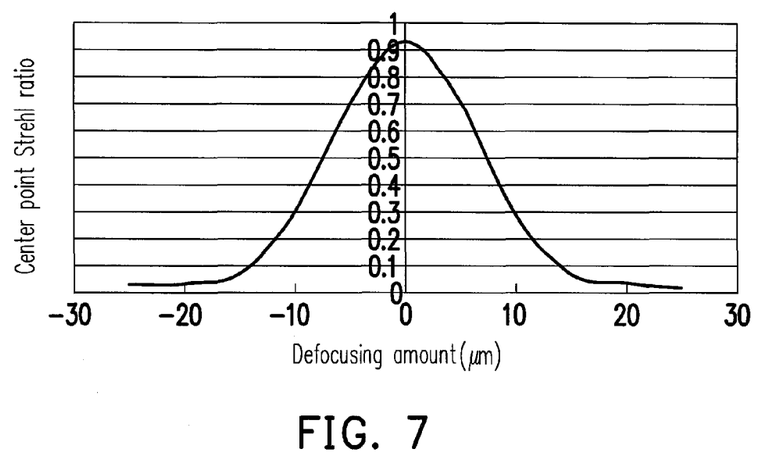
FIG. 7 is a schematic diagram illustrating a relationship of center point Strehl ratios and defocusing amounts of a conventional microscope system without a phase coding device.
Figure 8:
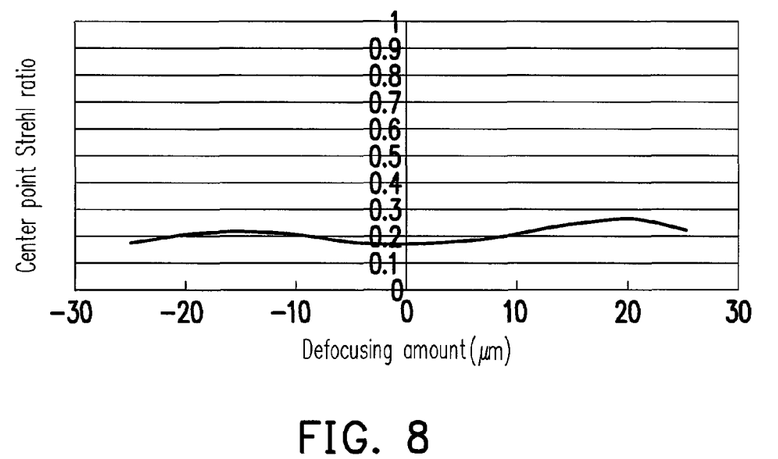
FIG. 8 is a schematic diagram illustrating a relationship of center point Strehl ratios and defocusing amounts of a microscope system with the phase coding device according to an embodiment of the disclosure.

An effect achieved by adding the axial symmetric phase coding device is described below. FIG. 7 is a schematic diagram illustrating a relationship of center point Strehl ratios and defocusing amounts of a conventional microscope system without the phase coding device. FIG. 8 is a schematic diagram illustrating a relationship of center point Strehl ratios and defocusing amounts of a microscope system with the phase coding device according to an embodiment of the disclosure.

Referring to FIG. 7, within a defocusing range of ±10 um of a conventional microscope, the center point Strehl ratios are below 0.2, and are unevenly distributed. The relationship of the center point Strehl ratios and the defocusing amounts has a large variation.

Referring to FIG. 8, the axial symmetric phase coding device is added, and within a defocusing range of ±25 um of the microscope with extended depth of field, the center point Strehl ratios are maintained to 0.2, and the depth of field can be extended by at least twice, and higher correlation is maintained.

Figure 9A:
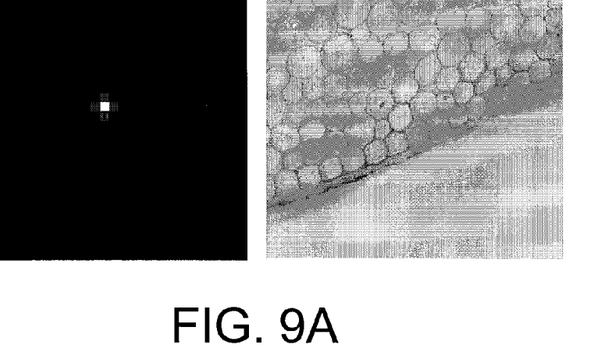
FIGS. 9A-9C are schematic diagrams of simulation images on a focal plane and defocusing planes of a conventional microscope system for phase object.
Figure 9B:
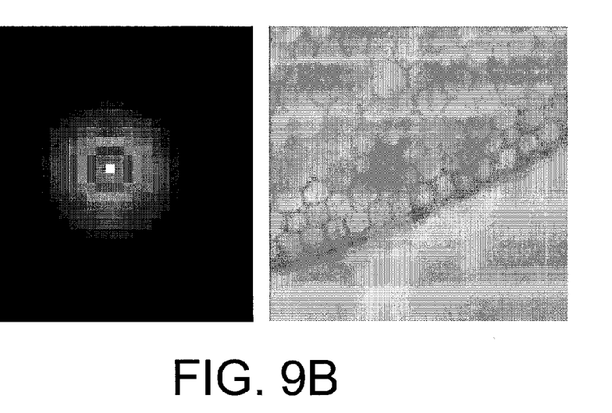
Figure 9C:
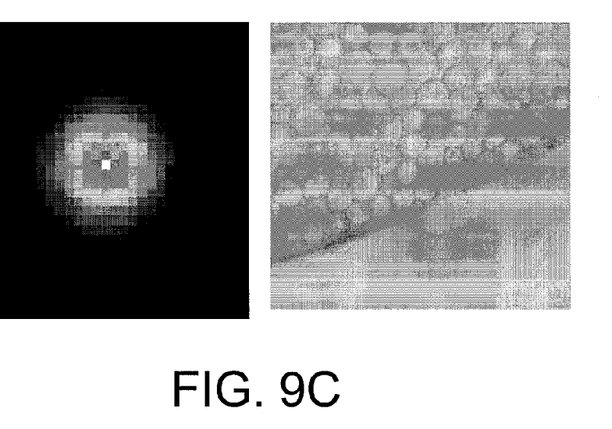

FIGS. 9A-9C are schematic diagrams of simulation images on a focal plane and defocusing planes of the conventional microscope system for phase object. Left parts of FIGS. 9A-9C are the PSF, and right parts are the simulation images. FIG. 9A illustrates an image on the focal plane. FIG. 9B illustrates an image on the defocusing plane of +25 um. FIG. 9C illustrates an image on the defocusing plane of −25 um. According to FIGS. 9A-9C, the images of FIG. 9B and FIG. 9C have a large variation relative to the image of FIG. 9A. A correlation of the images of FIG. 9B and FIG. 9A is 0.0432, and calculation of the correlation is described below. A correlation of the images of FIG. 9C and FIG. 9A is 0.031.

Figure 10A:
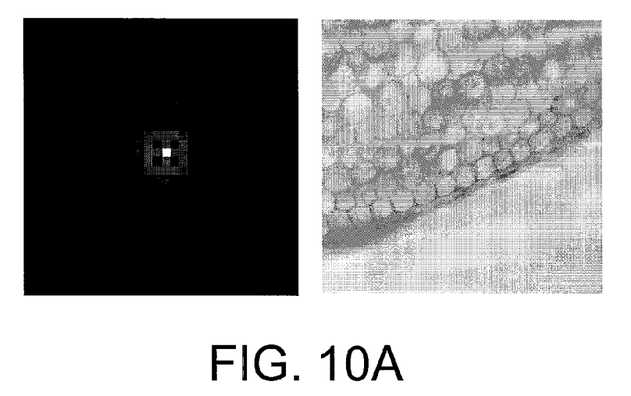
FIGS. 10A-10C are schematic diagrams of simulation images on a focal plane and defocusing planes of a microscope system with extended depth of field for phase object according to an embodiment of the disclosure.
Figure 10B:
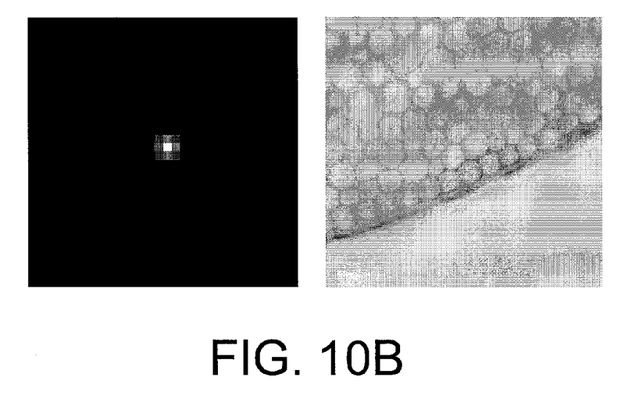
Figure 10C:
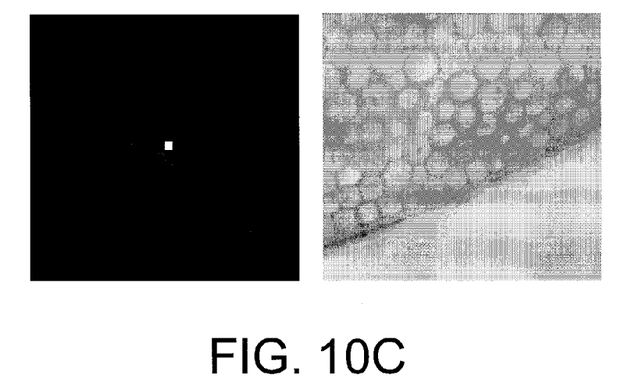

FIGS. 10A-10C are schematic diagrams of simulation images on a focal plane and defocusing planes of the microscope system for phase object according to an embodiment of the disclosure. Left parts of FIGS. 10A-10C are the PSF, and right parts are the simulation images. FIG. 10A illustrates an image on the focal plane. FIG. 10B illustrates an image on the defocusing plane of +25 um. FIG. 10C illustrates an image on the defocusing plane of −25 um. According to FIGS. 10A-10C, the images of FIG. 10B and FIG. 10C have a high similarity with the image of FIG. 10A. A correlation of the images of FIG. 10B and FIG. 10A is 0.832, and a correlation of the images of FIG. 10C and FIG. 10A is 0.948, which represents that the depth of field of the disclosure can be effectively increased, and correlation of the images is maintained.

Calculation of the correlation is described below with reference of an equation (8):

$$\text{Correlation} = \frac{\int_{-\infty}^{\infty}\int_{-\infty}^{\infty} PSF1(x,y)PSF2(x,y)dxdy}{\int_{-\infty}^{\infty}\int_{-\infty}^{\infty} PSF1(x,y)PSF1(x,y)dxdy}, \quad (8)$$

where, PSF1(x,y) is a PSF on the focal plane, and PSF2(x,y) is a PSF on the defocusing plane. Within a defocusing range of ±25 um of the conventional microscope, correlations of the PSF are all smaller than 0.1, and within a defocusing range of ±25 um of the microscope with extended depth of field of the disclosure, correlations of the PSF are all greater than 0.5.

The range of depth of field in the disclosure can be extended by twice compared to a diffraction limit depth of field of the system without the phase device.

The spherical aberration combination of the microscope system of the disclosure can be produced by itself or produced by using different external devices, and the external device can be a phase device, an axial symmetric aspherical lens, a diffraction optical device, a graded refractive index device, or a full spherical lens optical system, though the disclosure is not limited thereto.

The photoelectric converting device of the disclosure is, for example, an array-type photoelectric converting device, which can be further connected to an image restoration module, where the image restoration module restores a blurred image into a clear image by using an image restoration algorithm, so as to form a final image with extended depth of field.

The image restoration module can be a commonly used filter, for example, the image restoration module is an image restoration device having a minimum mean square error (MMSE) filter, which is used to restore images. In case of noises, a filter operation of the MMSE filter is represented by a following equation (9):

$$F(u,v) = \left[\frac{H^*(u,v)}{|H(u,v)|^2 + SNR(u,v)}\right]G(u,v), \quad (9)$$

where, u,v are spatial frequencies, G(u,v) is a blurred image, F(u,v) is a restored clear image, H(u,v) is an optical transfer function (OTF) of an optical system, SNR(u,v) is a signal to noise ratio of the optical system.

Besides the MMSE filter operation, the image restore module can also use a Wiener filter operation or a direct inverse filter operation.

The phase device that generates the spherical aberration can be disposed near the aperture, an entrance pupil plane, an exit pupil plane, near the entrance pupil plane or near the exit pupil plane.

According to another aspect, the microscope system for phase object may include an objective lens group, a tube lens group, an axial symmetric phase coding and a photoelectric converting device. The objective lens group has a predetermined range of depth of field, and captures an image light of a phase object. The tube lens group receives the image light output by the objective lens group, and converts the image light into a gathered image light. The axial symmetric phase coding is integrated in the objective lens group or disposed between the objective lens group and the tube lens group to produce an axial symmetric spherical aberration. The photoelectric converting device receives and converts the gathered image light output by the tube lens group to obtain a digital image.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An extended depth of field microscope system for phase object, comprising:
an optical imaging module, wherein an axial symmetric phase coding is added to an objective lens group to produce an axial symmetric spherical aberration, so as to obtain a point spread function and an image with extended depth of field with a predetermined level of correlation, wherein a correlation of the point spread function obtained according to the axial symmetric phase coding is at least more than 0.5; and a phase/intensity converting module, converting a phase variation of light passing through a phase object, due to optical path difference, into an image light with light intensity variation, wherein the axial symmetric phase coding is an axial irradiance equalization (AIE) phase coding f(r):

$$f(r) = \frac{f_0}{3} - \frac{\sqrt[3]{2}(3r^2 - f_0^2)}{3\left[2f_0^3 + 27Cr^2 + 18f_0r^2 + \sqrt{4(3r^2 - f_0^2)^3 + (2f_0^3 + 27Cr^2 + 18f_0r^2)^2}\right]^{1/3}} + \frac{\left[2f_0^3 + 27Cr^2 + 18f_0r^2 + \sqrt{4(3r^2 - f_0^2)^3 + (2f_0^3 + 27Cr^2 + 18f_0r^2)^2}\right]^{1/3}}{2(\sqrt[3]{2})},$$

where, $f_0$ is a paraxial focal length, r is an exit pupil radius, and C is defined by a following equation:

$$C = \frac{\Delta z[(R_{max})^2 + (f_0 + \Delta z)^2]}{(R_{max})^2},$$

where $\Delta z$ is a required range of a depth of focus, $R_{max}$ is a maximum exit pupil radius.

2. The extended depth of field microscope system for phase object as claimed in claim 1, wherein the microscope system has a range of depth of field by at least twice of a diffraction limit depth of field of the microscope system.

3. The extended depth of field microscope system for phase object as claimed in claim 1, wherein the spherical aberration comprises at least one third-order spherical aberration term.

4. The extended depth of field microscope system for phase object as claimed in claim 1, wherein the spherical aberration is produced by the objective lens group, or produced by an external optical device, wherein the optical device is a phase device, an axial symmetric aspherical lens, a diffraction optical device, a graded refractive index device, or a full spherical lens optical system.

5. The extended depth of field microscope system for phase object as claimed in claim 1, wherein the phase/intensity converting module is a transmissive differential interference contrast module comprising:
an illumination light source, providing an illumination light;
a polarizer, converting the illumination light into a linearly polarized light;
a first prism element, slitting the linearly polarized light into two polarized lights orthogonal to each other;
a condenser, converging the two polarized lights to the phase object to generate the image light;
a second prism element, combining the two polarized lights into a single light beam; and
a analyzer, receiving the single light beam, and converting the two polarized lights to a linearly polarized light.

6. The extended depth of field microscope system for phase object as claimed in claim 1, wherein the phase/intensity converting module is a reflective differential interference contrast module comprising:
an illumination light source, providing an illumination light;
a condenser, converging the illumination light;
a polarizer, converting the illumination light passing through the light converging lens into a linearly polarized light;
a beam splitter, reflecting the linearly polarized light to the phase object;
a prism element, splitting the linearly polarized light that passes through the prism element for a first time into two polarized lights orthogonal to each other, wherein the two polarized lights pass through the objective lens group and the axial symmetric phase coding, and are reflected by the phase object to have a phase difference, and are again pass through the objective lens group, the axial symmetric phase coding and the prism element, and the prism element recombines the two polarized lights into a single light beam; and
a analyzer, converting the two polarized lights orthogonal to each other to a linearly polarized light.

7. The extended depth of field microscope system for phase object as claimed in claim 1, wherein the phase/intensity converting module is a phase contrast module comprising:
an illumination light source, providing an illumination light;
a condenser, converging the illumination light;
an annulus plate, processing the illumination light to produce an annular light, wherein a first part of the annular light passes through the phase object, and a second part of the annular light does not pass through the phase object; and
a phase ring, producing a phase difference between the first part and the second part of the annular light to produce a destructive interference.

8. An extended depth of field microscope system for phase object comprising:
an optical imaging module, wherein an axial symmetric phase coding is added to an objective lens roup to produce an axial symmetric spherical aberration, so as to obtain a point spread function and an image with extended depth of field with a predetermined level of correlation, wherein a correlation of the point spread function obtained according to the axial symmetric phase coding is at least more than 0.5;
a phase/intensity converting module, converting a phase variation of light passing through a phase object, due to optical path difference, into an image light with light intensity variation;
a photoelectric converting device, receiving the image light, and converting the image light to obtain a digital image; and
an image restoration module, connected to the photoelectric converting device, and restoring the digital image into a clear image,
wherein the axial symmetric phase coding is an axial irradiance equalization (AIE) phase coding f(r):

$$f(r) = \frac{f_0}{3} - \frac{\sqrt[3]{2}(3r^2 - f_0^2)}{3\left[2f_0^3 + 27Cr^2 + 18f_0r^2 + \sqrt{4(3r^2 - f_0^2)^3 + (2f_0^3 + 27Cr^2 + 18f_0r^2)^2}\right]^{1/3}} +$$

-continued $$\frac{\left[2f_0^3 + 27Cr^2 + 18f_0r^2 + \sqrt{4(3r^2 - f_0^2)^3 + (2f_0^3 + 27Cr^2 + 18f_0r^2)^2}\right]^{1/3}}{2(\sqrt[3]{2})},$$

where, $f_0$ is a paraxial focal length, r is an exit pupil radius, and C is defined by a following equation:

$$C = \frac{\Delta z[(R_{max})^2 + (f_0 + \Delta z)^2]}{(R_{max})^2},$$

where $\Delta z$ is a required range of a depth of focus, $R_{max}$ is a maximum exit pupil radius.

9. The extended depth of field microscope system for phase object as claimed in claim 8, wherein the microscope system has a range of depth of field by at least twice of a diffraction limit depth of field of the microscope system.

10. The extended depth of field microscope system for phase object as claimed in claim 8, wherein the spherical aberration comprises at least one third-order spherical aberration term.

11. The extended depth of field microscope system for phase object as claimed in claim 8, wherein the spherical aberration is produced by the objective lens group, or produced by an external optical device, wherein the optical device is a phase device, an axial symmetric aspherical lens, a diffraction optical device, a graded refractive index device, or a full spherical lens optical system.

12. The extended depth of field microscope system for phase object as claimed in claim 8, wherein the image restoration module comprises a minimum mean square error filter, a Wiener filter or a direct inverse filter.

13. The extended depth of field microscope system for phase object as claimed in claim 8, wherein the phase/intensity converting module is a phase contrast module comprising:
 an illumination light source, providing an illumination light;
 a condenser, converging the illumination light;
 an annulus plate, processing the illumination light to produce an annular light, wherein a first part of the annular light passes through the phase object, and a second part of the annular light does not pass through the phase object; and
a phase ring, producing a phase difference between the first part and the second part of the annular light to produce a destructive interference for entering the photoelectric converting device.

14. The extended depth of field microscope system for phase object as claimed in claim 8, wherein the phase/intensity converting module is a transmissive differential interference contrast module comprising:
 an illumination light source, providing an illumination light;
 a polarizer, converting the illumination light into a linearly polarized light;
 a first prism element, slitting the linearly polarized light into two polarized lights orthogonal to each other;
 a condenser, converging the two polarized lights to the phase object to generate the image light;
 a second prism element, combining the two polarized lights into a single light beam; and
 a analyzer, receiving the single light beam, and converting the two polarized lights to a linearly polarized light.

15. The extended depth of field microscope system for phase object as claimed in claim 8, wherein the phase/intensity converting module is a reflective differential interference contrast module comprising:
 an illumination light source, providing an illumination light;
 a condenser, converging the illumination light;
 a polarizer, converting the illumination light passing through the light converging lens into a linearly polarized light;
 a beam splitter, reflecting the linearly polarized light to the phase object;
 a prism element, splitting the linearly polarized light that passes through the prism element for a first time into two polarized lights orthogonal to each other, wherein the two polarized lights pass through the objective lens group and the axial symmetric phase coding, and are reflected by the phase object to have a phase difference, and are again pass through the objective lens group, the axial symmetric phase coding and the prism element, and the prism element recombines the two polarized lights into a single light beam; and
 a analyzer, converting the two polarized lights orthogonal to each other to a linearly polarized light for entering the photoelectric converting device.

* * * * *